US008475445B2

(12) United States Patent
Soroff et al.

(10) Patent No.: US 8,475,445 B2
(45) Date of Patent: Jul. 2, 2013

(54) SPECTRAL ANALYSIS OF INTRACARDIAC ELECTROGRAMS TO PREDICT IDENTIFICATION OF RADIOFREQUENCY ABLATION SITES

(76) Inventors: Daniel Soroff, Cumberland Foreside, ME (US); David Kaczka, Baltimore, MD (US)

(*) Notice: Subject to any disclaimer, the term of this patent is extended or adjusted under 35 U.S.C. 154(b) by 664 days.

(21) Appl. No.: 12/628,583

(22) Filed: Dec. 1, 2009

(65) Prior Publication Data
US 2010/0137861 A1 Jun. 3, 2010

Related U.S. Application Data

(60) Provisional application No. 61/118,718, filed on Dec. 1, 2008.

(51) Int. Cl.
*A61B 18/18* (2006.01)
(52) U.S. Cl.
USPC .............................. 606/34; 607/122; 600/374
(58) Field of Classification Search
USPC 600/374, 515; 606/34, 41; 607/122; 128/898
See application file for complete search history.

(56) References Cited

U.S. PATENT DOCUMENTS

| 5,792,064 | A | * | 8/1998 | Panescu et al. | 600/510 |
| 6,088,614 | A | * | 7/2000 | Swanson | 600/510 |
| 6,236,883 | B1 | * | 5/2001 | Ciaccio et al. | 600/515 |
| 7,245,962 | B2 | * | 7/2007 | Ciaccio et al. | 600/512 |
| 8,010,186 | B1 | * | 8/2011 | Ryu | 600/509 |
| 8,216,228 | B2 | * | 7/2012 | Pachon Mateos et al. | 606/41 |
| 2006/0122526 | A1 | * | 6/2006 | Berenfeld et al. | 600/515 |

OTHER PUBLICATIONS

Sanders et al., "Spectral Analysis Identifies Sites of High-Frequency Activity Maintaining Atrial Fibrillation in Humans" Circulation, www.circulationaha.org, Aug. 9, 2005, pp. 789-797.

* cited by examiner

*Primary Examiner* — Linda Dvorak
*Assistant Examiner* — Jocelyn D Ram
(74) *Attorney, Agent, or Firm* — Gesmer Updegrove LLP

(57) ABSTRACT

A method and system for choosing suitable sites for catheter delivery ablative energy is provided that includes a catheter/ablation structure that is positioned on a potential ablation site on a heart. The catheter/ablation structure produces one or more electrograms recorded at the potential ablation site. A signal processing unit receives from the catheter/ablation structure the recorded one or more intercardiac electrograms from the potential ablation site and performing Fast Fourier Transform (FFT) on the recorded one or more intercardiac electrograms as so to produce one or more spectral power distributions of the potential ablation site. A display unit displays the one or more spectral power distributions so as to determine whether the potential RF ablation site exhibit necessary spectral properties for the delivery of the ablative energy. A ablative energy generator unit provides the ablative energy to the potential ablation site using the catheter/ablation structure.

8 Claims, 5 Drawing Sheets

⇨ = depolarizing wavefront

ID OF RADIOFREQUENCY
SPECTRAL ANALYSIS OF INTRACARDIAC ELECTROGRAMS TO PREDICT IDENTIFICATION OF RADIOFREQUENCY ABLATION SITES

PRIORITY INFORMATION

This application claims priority from provisional application Ser. No. 61/118,718 filed Dec. 1, 2008, which is incorporated herein by reference in its entirety.

BACKGROUND OF THE INVENTION

The invention is related to the field of radiofrequency (RF) ablation, and in particular to using Fourier analysis of intracardiac electrograms to assess whether their spectral power distributions could be used to predict ablation sites most likely to result in ventricular tachycardia (VT) termination or termination of other reentrant tachycardia circuits, such as atrioventricular nodal reentrant tachycardia (AVNRT), paroxysmal junctional reciprocating tachycardia (PJRT), or atrioventricular reentrant tachycardias (AVRT) with midseptal accessory pathways, in which the rapidly and slowly conducting limbs of the reentrant circuit lie in close physical proximity to one another.

Ventricular tachycardia (VT), a potentially lethal cardiac arrhythmia, can arise from several different mechanisms. Idiopathic VT is believed to arise from enhanced automaticity, and can often occur in the absence of any apparent structural heart disease. More commonly, VT results from reentry phenomena in association with a narrow isthmus of abnormally conducting tissue that traverses a scar (or scar border) caused by myocardial infarction or other injury. Following such injury, one or more isthmi of abnormally conducting tissue 2 can be located between islands of unexcitable scar tissue 4, or adjacent to some other functionally unexcitable boundary such as a valve annulus, as shown in FIG. 1. Such an isthmus 2 is referred to as the "protected isthmus," or slow conduction zone, and is critical to the formation of a tachycardia circuit that can support sustained reentry. Rapid conduction zone 6 is associated with normal myocardium and the rapid and slow conduction zones are clearly illustrated using depolarizing wavefronts 8. This substrate can give rise to monomorphic ventricular tachycardia, as judged by both surface and intracardiac electrograms. Thus, monomorphic reentrant ventricular tachycardias (VT) can theoretically occur even if one protected isthmus forms in a scar-related re-entry circuit.

While the current standard of care for the management of most ischemic or scar-related VT is the implantable cardioverting defibrillator (ICD), a significant number of patients with frequent or incessant VT undergo radiofrequency (RF) ablation (or ablation using another lesion generating energy such as cryoablation) of their scar-related substrate. This is usually performed to minimize the number of ICD therapies received by patients who have frequent arrhythmia recurrences despite treatment with medication. Greater than 75% of patients referred for palliative ablation of arrhythmias will have fewer VT recurrences. Less commonly, RF ablation of scar-related VT is performed as first-line therapy for patients with relatively normal LV systolic function and a single known VT substrate.

Recently, there has been renewed interest in VT ablation to prevent or minimize the likelihood of appropriate defibrillator therapies in order to improve patient morbidity and mortality. Catheter ablation of VT may assume an even greater relevance in light of recent studies that demonstrate increased mortality in patients with congestive heart failure that receive frequent shocks from an implanted defibrillator for primary prevention of sudden arrhythmic death.

Several methods are available to identify the location of the VT circuit during ablation procedures. The ability to demonstrate concealed entrainment (with a paced morphology identical to the VT) from a site can be used to determine whether the ablation catheter tip is in direct contact with tissue that contributes to a VT circuit. Commercially available manual and remote three dimensional electroanatomical mapping systems can also be used to create voltage, substrate, and activation sequence maps of the VT circuit. Electrically Unexcitable Scar (EUS) mapping (mapping of pacing thresholds), the presence of late potentials, and electroanatomical mapping can all be used to localize the protected isthmus.

Within the VT circuit, it is important to identify the protected isthmus (slow conduction zone) as the target for the delivery of RF or other ablative energy such as cryoablation or ultrasound ablation lesions. If lesions are not applied at locations within the isthmus (i.e. if they do not connect the unexcitable tissue that bounds the isthmus), then the lesion is likely to only extend the region of scar into otherwise healthy myocardium, and will fail to close the VT circuit. This is probably important in the patient population undergoing scar-related VT ablation procedures, as their ventricular systolic function is often already significantly impaired.

This technique same could be employed to identify the slow conduction zone, or slow limb, of other reentrant tachycardia circuits in which the rapidly and slowly conducting limbs of the reentrant circuit lie in close physical proximity to one another, such as atrioventricular nodal reentrant tachycardia, paroxysmal junctional reciprocating tachycardia, or atrioventricular reentrant tachycardias with midseptal accessory pathways.

SUMMARY OF THE INVENTION

According to one aspect of the invention, there is provided a method for choosing suitable sites for catheter delivery ablation. The method includes providing a catheter/ablation structure that is positioned on a potential ablation site on a heart. Also, the method includes receiving from the catheter/ablation structure one or more intercardiac electrograms recorded from the potential ablation site. A Fast Fourier Transform (FFT) is performed on the recorded one or more intercardiac electrograms to produce one or more spectral power distributions of the potential ablation site. In addition, the method includes the display of the spectral power distributions, so as to determine whether the ablation site exhibits necessary spectral properties for the delivery of ablative energy. Furthermore, the method includes providing ablative energy to the potential ablation site once it has been determined that the potential ablation site exhibits the necessary spectral properties.

According to another aspect of the invention, there is provided a system for choosing suitable sites for catheter delivery of ablative energy. The system includes a catheter/ablation structure that is positioned on a potential ablation site on a heart. The catheter/ablation structure produces one or more electrograms recorded at the potential ablation site. A signal processing unit receives from the catheter/ablation structure the recorded one or more intercardiac electrograms from the potential ablation site and performs Fast Fourier Transform (FFT) on the recorded one or more intercardiac electrograms as so to produce one or more spectral power distributions of the potential ablation site. A display unit displays the one or more spectral power distributions so as to determine whether the potential ablation site exhibit necessary spectral properties for the delivery of RF or other ablative energy. An ablative energy generator unit provides energy to the potential ablation site using the catheter/ablation structure once it has been determined that the potential ablation site exhibits the necessary spectral properties.

DETAILED DESCRIPTION OF THE INVENTION

The invention provides a technique where spectral power distributions of electrograms recorded at ablation sites can be used to predict ablation sites most likely to result in ventricular tachycardia (VT) termination or termination of other reentrant tachycardia circuits in which the rapidly and slowly conducting limbs of the reentrant circuit lie in close physical proximity to one another.

Figure 1:
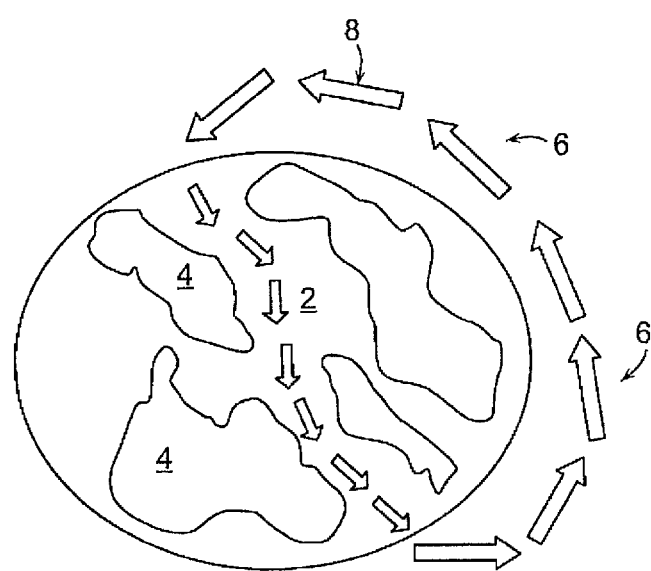
FIG. 1 is a schematic diagram illustrating a scar-related, re-entrant VT circuit.
Figure 2A:
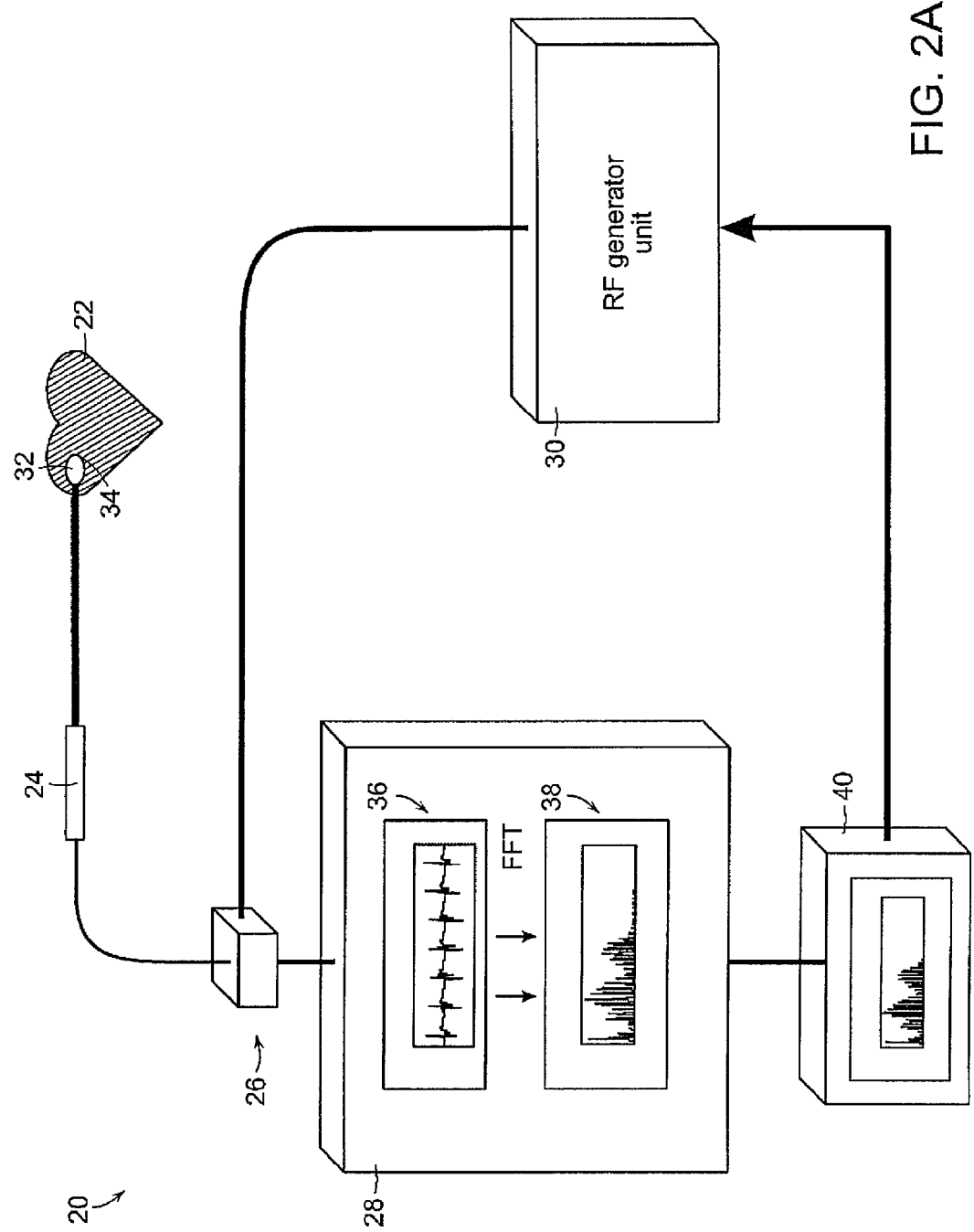
FIG. 2A is a schematic diagram illustrating the inventive system used in predicting ablation sites most likely to result in VT termination.

FIG. 2A is a schematic diagram illustrating the inventive system 20 used in predicting ablation sites most likely to result in VT termination. VT is used as an example of a tachycardia circuit in which the rapidly and slowly conducting limbs of the reentrant circuit lie in close physical proximity to one another. The system 20 includes a catheter/ablation structure 24 having a probe 32 positioned on an ablation site 34 on a heart. The catheter/ablation structure 24 produces local intracardiac electrograms 36 recorded at the ablation site 34 and sends the recorded local intracardiac electrograms 36 to an adaptor port 26 where it is sent to a signal processing unit 28. The adaptor port 26 regulates the flow of information from the catheter/ablation structure 24 to the signal processing unit 28 as well as providing the catheter/ablation structure 24 with ablative energy from an ablative energy generator unit 30 to be applied on the ablation site 34. Once the signal processing unit 28 receives the recorded electrograms 36, it further performs a Fast Fourier transform (FFT) of the recorded electrograms 36 to produce spectral power distributions 38 for spectral analysis. The spectral power distributions 38 are provided to a display unit 40 so as to allow one to determine whether VT termination can be accomplished for that particular ablation site 34. Once it has been determined that the ablation site 34 meets the criteria for VT termination, the adaptor 26 allows the catheter/ablation structure 24 to receive ablative energy from the ablative energy generator unit 30 to be applied on the ablation site 34.

The ablative energy generator unit can produce RF energy or other ablative energy such as cryoablation or ultrasound ablation lesions.

Figure 2B:
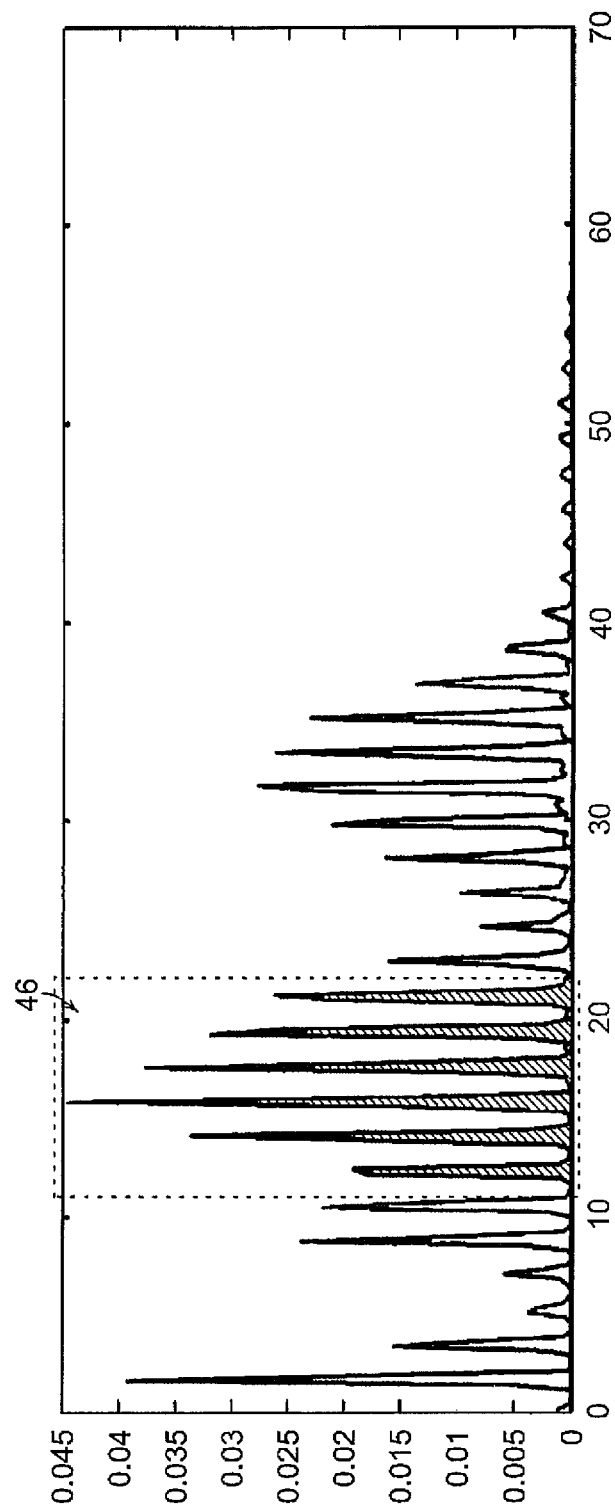
FIG. 2B is a schematic diagram illustrating a visual display produced by the invention.

The signal processing unit 28 can include a digital to analog converter, other hard-wired device, or software that generates a Fast Fourier Transform of the recorded electrograms 36 within the 0-1000 Hertz range. Also, the signal processing unit 28 stores the recorded electrograms 36 for further FFT processing. The display unit 40 can enhance a specific segment of this frequency range with color, magnification, or contrast for the purpose of highlighting an enhancement window 46 of the spectrum as a visual aid, as shown in FIG. 2B. Also, the display unit 40 can allow an operator to display or select the frequency around which the enhancement window 46 is centered. The width of the enhancement window 46 can be displayed or adjusted by an operator using the display unit 40. The width and center of the enhancement window 46 can be adjusted by an operator using a dialing structure or other adjustment means.

In other embodiments of the invention, the display unit 40 can be incorporated into the signal processing unit 28 as a single unit. Moreover, the signal processing unit 28 can be separate units where the FFT can be performed by a spectral analysis unit that retrieves the recorded electrograms 36 from a separate storage device for processing.

The invention compares the spectral power distributions of the electrograms that are recorded at RF ablation sites that successfully terminated VT, with those that were recorded at RF sites that did not successfully terminate VT. The purpose of this was to assess whether a unique spectral pattern can predict termination of VT with the application of an RF lesion at that site. Other types of lesions can be used such as cryoablation and ultrasound lesions.

Figure 3:
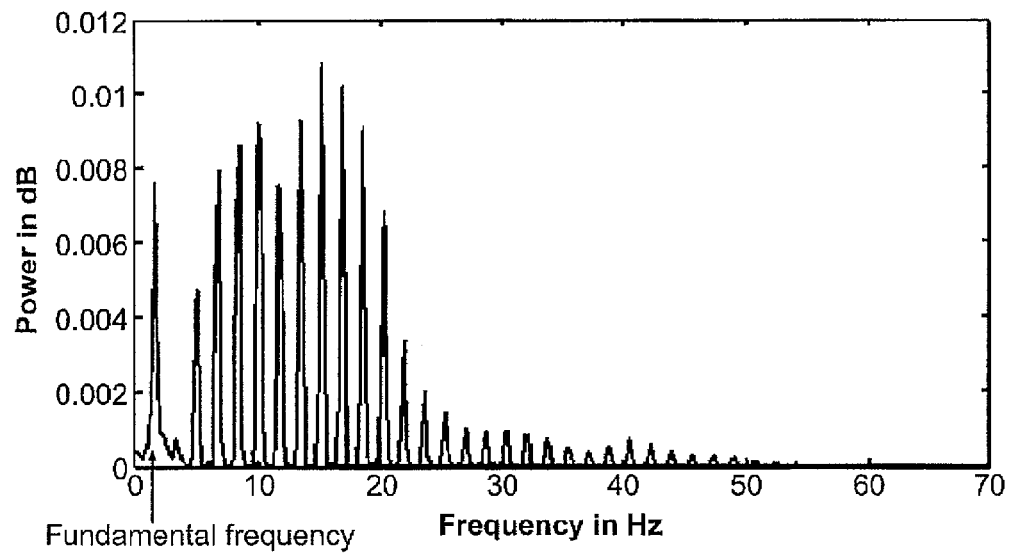
FIG. 3 is a graph illustrating unimodal power spectra of an intracardiac electrogram recorded at the site of a VT-terminating ablation lesion.
Figure 4:
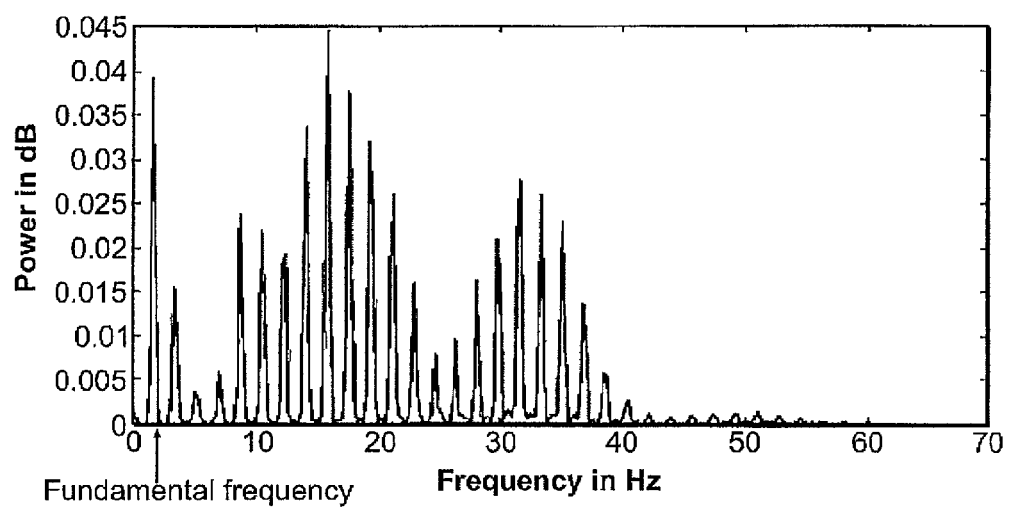
FIG. 4 is a graph illustrating bimodal power spectra of an intracardiac electrogram recorded at the site of a non-VT-terminating ablation lesion.

The RF ablation sites that have successfully terminate VT are likely to have spectral distributions which are nearly unimodal (discounting the carrier frequency), and have most of their power in the low frequency range of the spectrum, as shown in FIG. 3. The explanation for this seems to be that the application of sufficient RF energy in these regions results in conduction block within the protected VT isthmus. The additional data obtained using CARTO maps support this notion. The fact that terminating RF energy have a high power output in the low frequency region of the spectrum, also probably corresponds to the presence of diastolic potentials (or low frequency signals) at that site. Conversely, non-terminating RF sites were more likely to demonstrate bimodal spectral distributions as shown in FIG. 4.

This is consistent with the notion that non-terminating ablation sites are likely to be at the junction of rapidly conducting (high frequency) and slowly conducting (low frequency) tissue zones. The percentage of lesions that were correctly judged to be terminating based on the spectral features of the electrogram at the lesion site, ranged from 64% to 91% for twenty runs through the data. The mean percentage correct was 79%. The mean positive predictive value for an RF lesion to be a terminating RF lesion, given that it was judged as having a unimodal spectral pattern by a blinded observer, was 72%.

The presence of a bimodal spectral power distribution at an RF ablation site reflects the existence of both fast conducting and slow conducting zones of tissue at that site. Application of RF energy at such a site is unlikely to terminate VT probably because it merely extends the area of scar, rather than closing the isthmus, and thereby leaves an intact, anatomically larger, reentry circuit.

Figure 5:
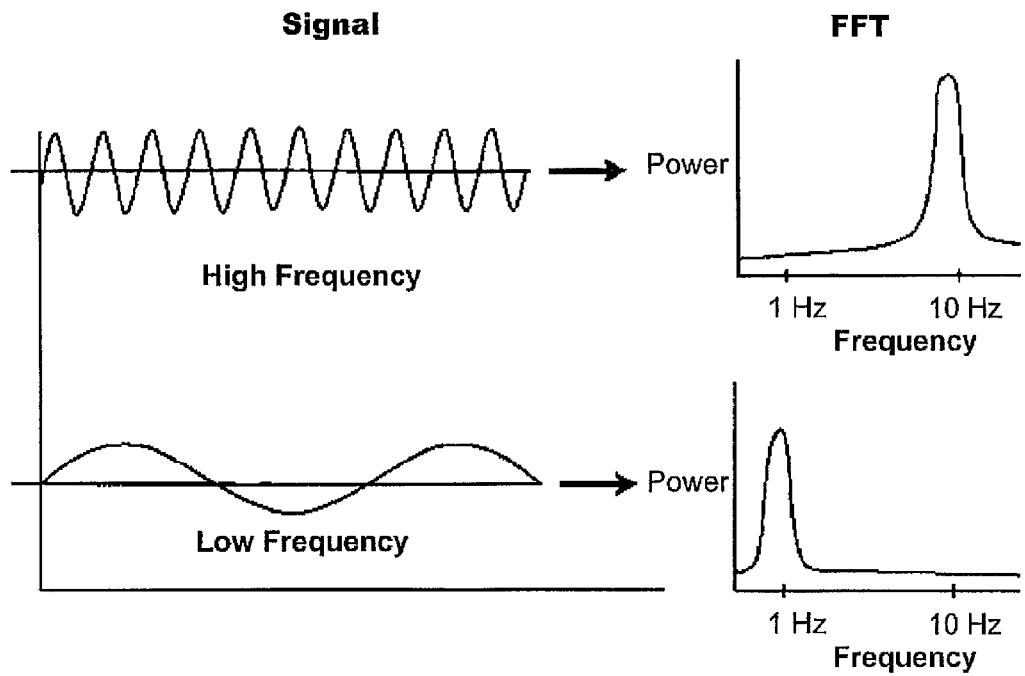
FIG. 5 is a schematic diagram illustrating power spectra of high and low frequency waveforms.

A fast pathway of a VT circuit can be interpreted as representing high frequency components of the circuit. In contrast to a slow pathway, or protected isthmus, represents its low frequency component. To appreciate this, one can imagine an entire circuit that is composed of fast pathway tissue. This circuit would have a higher frequency, and a narrower electrogram, than an identical imaginary circuit composed entirely of slow pathway tissue which would have a "wide" electrogram. Thus narrow electrograms correspond to high spectral frequencies, and wide electrograms correspond to low spectral frequencies, as shown in FIG. 5.

Figure 6:
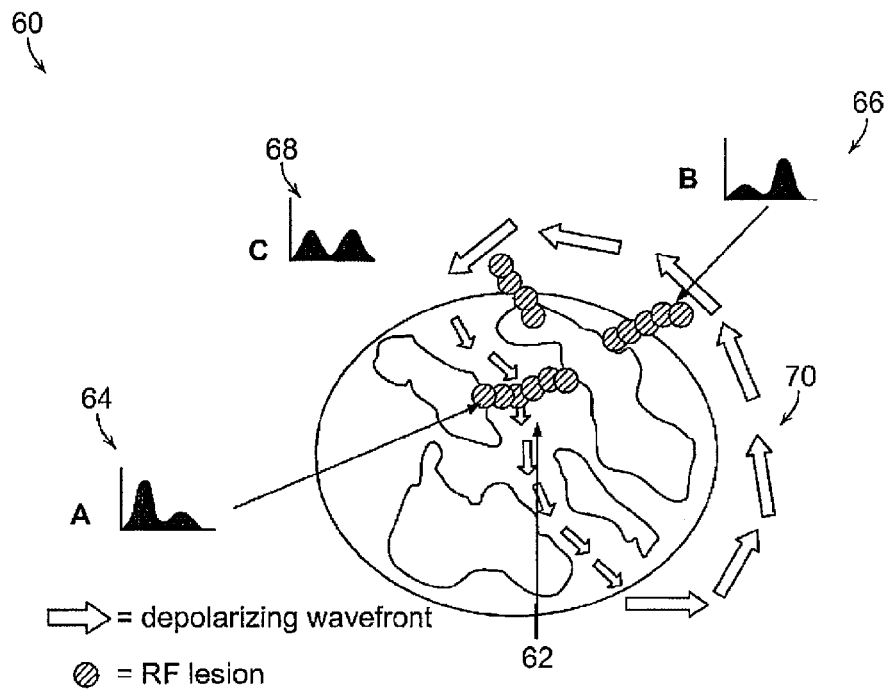
FIG. 6 is schematic diagram illustrating a scar-related, re-entrant VT circuit with corresponding electrogram power spectra at different locations.

FIG. 6 is a schematic diagram illustrating a scar-related, re-entrant VT circuit 60 with corresponding electrogram power spectra at different locations. In particular FIG. 6 shows a Zone A illustrating low conduction zone; Zone B illustrating rapid conduction zone; and Zone C illustrating junction of slow and rapid conduction zones. It follows that an electrogram from a catheter tip positioned in the protected isthmus 62 of the circuit 60, where conduction velocity is slowed, would result in a spectral distribution 64 with a large amount of power in the low frequency range, as shown in Zone A. Conversely, an electrogram from a catheter tip positioned in the fast limb of the circuit, where a rapid conduction zone 70, would result in a spectral distribution 66 with a large amount of power in the high frequency range, as shown in Zone B. Both of these distributions 64, 66 have "unimodal" frequency distribution patterns (i.e. unimodal-high and unimodal-low patterns). A catheter tip placed at the junction of the slow and fast limbs of the circuit 60 (which occur at both the "entry" and "exit" sites to and from the circuit), is likely to have a spectral distribution 68 in both the high and low frequency ranges of the spectrum, as shown in Zone C. This distribution is therefore bimodal.

It is important to note that there will always be high power output at the frequency which corresponds to the actual rate of the tachycardia. For example, if the rate of the tachycardia is 120 bpm (or two beats per second), then there will be a high power output at 2 Hz. This is known as the "fundamental frequency," and it merely results in a shift of the spectral distribution across the frequency range, regardless of whether it is unimodal, bimodal, or multi-modal.

There is a good possibility that real-time spectral analysis of electrograms can decrease VT ablation procedure times, which holds the promise of lowering costs, limiting exposure to ionizing radiation for both the patient and the operator, and decreasing the use of sedative medications which transiently depress cardiopulmonary function. Moreover, spectral analysis might limit the average number of RF lesions delivered to the ventricle during VT ablation procedures. This would possibly benefit a patient population that frequently has baseline impairment of left ventricular systolic function.

In addition, it is possible that a spectral analysis of intracardiac electrograms could also aid in the localization of the slowly conducting tissue within other types of reentrant circuits with closely juxtaposed fast and slow limbs. For example, the same methods used in the current study might facilitate the radiofrequency ablation of atrioventricular nodal reentrant tachycardia, paroxysmal junctional reciprocating tachycardia, or atrioventricular reentrant tachycardias with midseptal accessory pathways.

The results produced by the invention suggest that the pattern of the frequency spectra of intracardiac electrograms recorded at the tip of the catheter/ablation structure during ablation of reentrant, scar related VT, are useful for targeting sites for ablation. Power spectra of electrograms from sites that possess unimodal low frequency distributions demonstrate considerable positive predictive value for the successful termination of VT using RF ablation.

Although the present invention has been shown and described with respect to several preferred embodiments thereof, various changes, omissions and additions to the form and detail thereof, may be made therein, without departing from the spirit and scope of the invention.

What is claimed is:

1. A method of choosing suitable sites for catheter delivery of ablative energy comprising:
   providing a catheter/ablation structure that is positioned on a potential ablation site on a heart;
   receiving from the catheter/ablation structure one or more intercardiac electrograms recorded from the potential ablation site;
   performing Fast Fourier Transform (FFT) on the recorded one or more intercardiac electrograms so as to produce one or more spectral power distributions of the potential ablation site;
   displaying the one or more spectral power distributions so as to determine whether the potential ablation site exhibits necessary spectral properties for the delivery of the ablative energy; and
   providing the ablation energy to the potential ablation site once it has been determined that the potential ablation site exhibits the necessary spectral properties, the necessary spectral properties aid in determining if the potential ablation site is a ventricular tachycardia (VT) termination site having power distributions that are nearly unimodal or a slow pathway site for other reentrant tachycardia circuits in which the rapidly and slowly conducting limbs of the reentrant circuit lie in physical proximity to one another.

2. The method of claim 1, wherein the step of receiving from the catheter/ablation structure one or more recorded intercardiac electrograms comprises using a storage unit.

3. The method of claim 1, wherein the step of performing FFT comprises using a digital to analog converter or software.

4. The method of claim 1, wherein the step of displaying the one or more spectral power distributions comprises enhancing a specific segment of a frequency range with color, magnification, or contrast.

5. The method of claim 1, wherein the step of displaying the one or more spectral power distributions comprises allowing an operator to display or select the frequency around where an enhancement window is centered.

6. The method of claim 5, wherein the step of displaying the one or more spectral power distributions comprises adjusting the width and center of the enhancement window.

7. The method of claim 1, wherein the recorded one or more intercardiac electrograms comprise a frequency between 0 and 1000 Hz.

8. The method of claim 1 wherein the catheter/ablation structure produces an ablative lesion at the potential ablation site to successfully terminate VT using the ablative energy.

* * * * *